United States Patent
McKee et al.

(10) Patent No.: US 9,664,646 B2
(45) Date of Patent: May 30, 2017

(54) POLYACRYLAMIDE ELECTROPHORESIS GELS WITH PROTECTION AGAINST OXYGEN EXPOSURE

(71) Applicant: Bio-Rad Laboratories, Inc., Hercules, CA (US)

(72) Inventors: Jason McKee, Martinez, CA (US); Cory Panattoni, Winters, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 445 days.

(21) Appl. No.: 14/085,472

(22) Filed: Nov. 20, 2013

(65) Prior Publication Data

US 2014/0138248 A1    May 22, 2014

Related U.S. Application Data

(60) Provisional application No. 61/728,366, filed on Nov. 20, 2012.

(51) Int. Cl.
*G01N 27/447* (2006.01)
*B29C 45/16* (2006.01)
*G01N 27/453* (2006.01)

(52) U.S. Cl.
CPC . *G01N 27/44747* (2013.01); *G01N 27/44756* (2013.01); *G01N 27/453* (2013.01)

(58) Field of Classification Search
CPC .......... G01N 27/44747; B29C 45/1679; B29C 70/882
See application file for complete search history.

(56) References Cited

U.S. PATENT DOCUMENTS

| | | |
|---|---|---|
| 4,897,306 A | 1/1990 | Sugimoto et al. |
| 5,685,967 A | 11/1997 | Manis et al. |
| 5,753,095 A | 5/1998 | Alpenfels et al. |
| 6,846,881 B2 | 1/2005 | Panattoni |
| 2008/0128281 A1 | 6/2008 | Blikstad et al. |
| 2009/0312462 A1 | 12/2009 | Oakley et al. |
| 2010/0227094 A1* | 9/2010 | Levesque ............... B29C 45/14 428/36.7 |
| 2011/0045222 A1 | 2/2011 | Peters |
| 2013/0264743 A1* | 10/2013 | Urushidani ....... B29C 45/14688 264/279 |

FOREIGN PATENT DOCUMENTS

WO    90/13020 A1    11/1990

OTHER PUBLICATIONS

The International Search Report and Written Opinion from PCT/US2013/071079, dated Mar. 25, 2014.

* cited by examiner

*Primary Examiner* — Gurpreet Kaur
(74) *Attorney, Agent, or Firm* — Kilpatrick Townsend & Stockton LLP

(57) ABSTRACT

The detrimental effect of oxygen exposure on the formation of polyacrylamide electrophoresis gels in oxygen-permeable plastic cassettes is reduced or eliminated either by the use of an oxygen barrier material over the surfaces of the plastic walls of the cassette through which oxygen would otherwise pass into the cassette cavity, or by the incorporation of an oxygen scavenger in the plastic from which the cassette walls are made, or both.

12 Claims, 1 Drawing Sheet

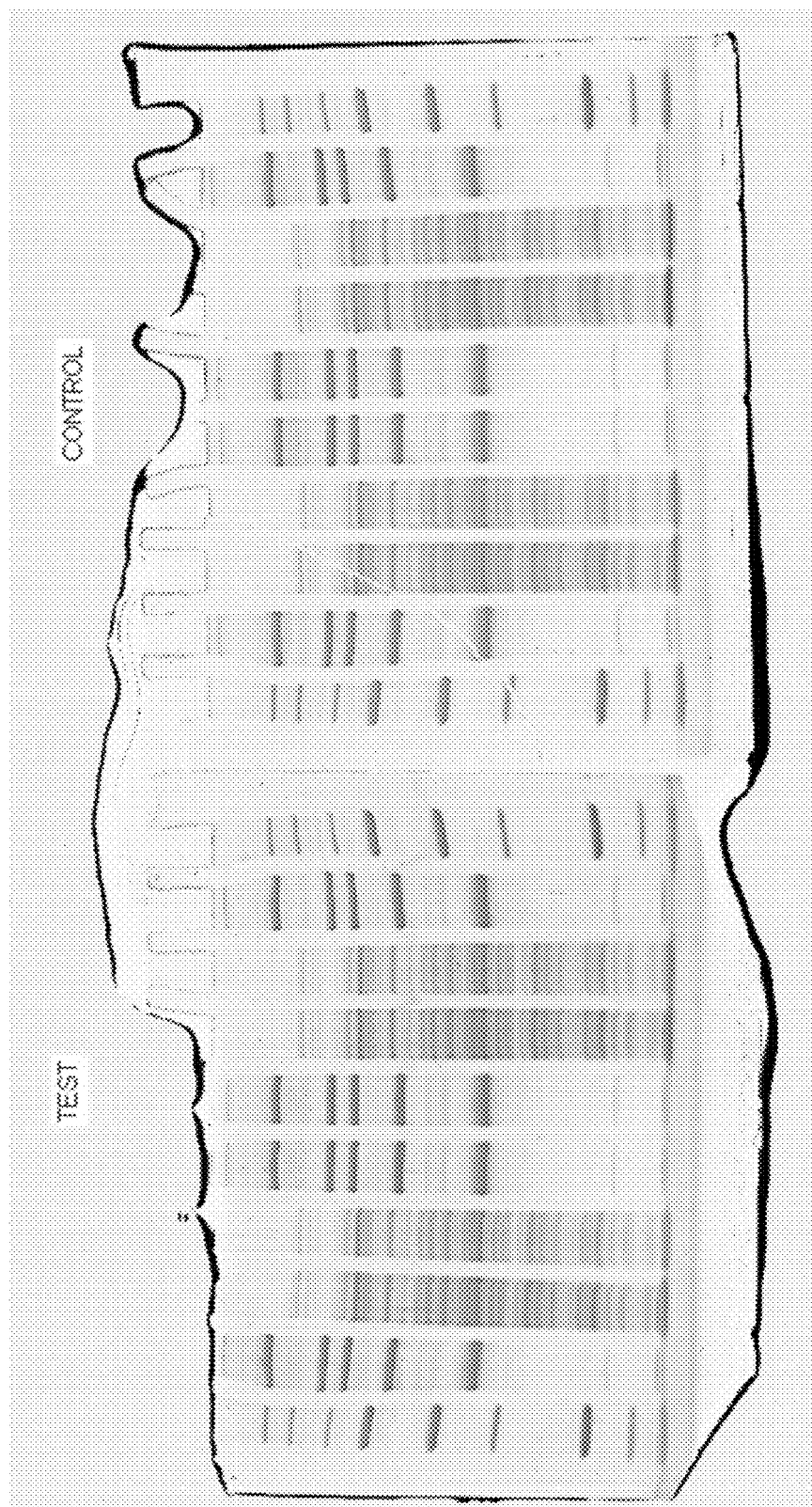

POLYACRYLAMIDE ELECTROPHORESIS GELS WITH PROTECTION AGAINST OXYGEN EXPOSURE

CROSS-REFERENCES TO RELATED APPLICATIONS

The present application claims priority to U.S. Provisional Patent Application No. 61/728,366, entitled "POLYACRYLAMIDE ELECTROPHORESIS GELS WITH PROTECTION AGAINST OXYGEN EXPOSURE" and filed Nov. 20, 2012, which is incorporated by reference herein in its entirety for all purposes.

BACKGROUND OF THE INVENTION

1. Field of the Invention

This invention resides in the field of polyacrylamide gels for use in electrophoresis, and particularly in the casting of such gels in plastic cassettes.

2. Description of the Prior Art

Polyacrylamide gel electrophoresis is widely used in biotechnology laboratories for the processing of biological samples to separate biomolecules present in the samples for identification and sometimes for quantitation and analysis. Protein mixtures, peptide mixtures, and mixtures of DNA, RNA, and fragments of DNA and RNA can all be separated on polyacrylamide gels. Slab-shaped gels are particularly useful in view of their ability to accommodate multiple separations performed simultaneously in parallel lanes, and to accommodate two-dimensional separations in which complex mixtures can be subjected to two different separation conditions in sequence. Slab-shaped gels also offer ease of detection of the separated species, both visually and by automated means, with or without removal of the gels from their retaining structures. Slab gels are commonly held in cassettes, which are transparent enclosures that provide dimensional stability to the gels, facilitate the loading of samples onto the gels, and allow electrical connections to be made so that electrophoretic procedures can be performed, all without the user touching the gel. Cassettes are also useful for holding precast gels, which can save time in the laboratory and provide both quality control and uniformity, particularly when the precast gel is prepared by a supplier rather than the user.

The typical slab gel cassette consists of two flat plates joined together along two opposing edges either by adhesives, chemical welding, sonic welding, or laser welding, with spacers at the edges to leave a slab-shaped cavity between the plates for the gel. When cassettes were originally manufactured, the plates were made of glass whose transparency and inertness made it easy to monitor the progress of the electrophoresis and to detect the bands of the separated biomolecules. Glass is expensive and fragile however and imposes limits on the design and shape of the cassette. This has led to the use of plastics, which not only avoid these problems but also offer the advantage of being readily formed to any shape by injection molding. The difficulty with plastics however is that plastics are permeable to oxygen. Cassette walls that are permeable to atmospheric oxygen expose the monomer solution from which the gel is cast to oxygen. This inhibits polymerization, and the result is often a defective gel, or at the least a high risk of nonuniformity in the porosity and density of the gel across the length and width of the slab.

SUMMARY

The problem of oxygen-related inhibition of the polymerization of acrylamide monomer in a plastic cassette is addressed herein by inhibiting oxygen access to the cassette cavity and thereby to the monomer solution. This is achieved by the introduction of two materials to the cassette, either individually as alternatives or in combination. The first such material is an oxygen barrier material in the form of a layer placed over the cassette walls, and the second is an oxygen scavenger substance embedded within the matrix plastic that forms the walls of the cassette. The cassette walls that either are covered with the oxygen barrier layer or contain the embedded oxygen scavenger will be all such walls that are wetted by the monomer solution during polymerization, or in certain embodiments of the invention, all walls that border the cassette cavity in which the monomer solution is placed, including any portions of the cavity that may be reserved as a head space above the monomer solution. In still further embodiments, the entire cassette will be covered with the oxygen barrier layer or contain the embedded oxygen scavenger, including portions of the cassette that do not contact the monomer solution or border the cavity but may perhaps be used for support of the cassette in an electrophoresis cell, or for electrical connections, or for placing buffer solutions (or the electrode chambers in which the solutions reside) in contact with the upper and lower edges of the gel during an electrophoresis procedure. Disclosed herein are the structure and composition of cassettes themselves that meet these descriptions, as well as methods of forming a polyacrylamide gel within such cassettes, and methods of use of such cassettes in polyacrylamide gel electrophoresis, notably SDS-PAGE. The descriptions herein are of value to all polyacrylamide gels in plastic cassettes, with particular interest for slab gels, and particular interest as well for pre-cast slab gels.

A combination of a polyacrylamide gel and a plastic cassette in which the polyacrylamide gel resides is provided. The plastic cassette includes: cassette walls enclosing a gel cavity and including a matrix plastic that is permeable to oxygen; and, means for inhibiting oxygen access to the polyacrylamide gel through the cassette walls, the means including either (i) an oxygen barrier layer covering walls of the cassette, (ii) an oxygen scavenger embedded within the matrix, or (iii) both (i) and (ii).

In some embodiments, means for inhibiting oxygen access to the polyacrylamide gel through the cassette walls comprise an oxygen barrier layer covering walls of said cassette. In one such embodiment, the oxygen barrier layer covers all surfaces of the cassette walls that are in contact with the polyacrylamide gel. In another such embodiment, the oxygen barrier layer is a layer of polyvinylidene chloride, low-density polyethylene, or an acrylonitrile methyl acetate copolymer. In yet another such embodiment, the oxygen barrier layer has an oxygen permeability at 25° C. and 100% RH of $5 \times 10^{-10}$ $[cm^3 \, cm]/[cm^2 \, s \, (cm \, Hg)]$ or less. In still another such embodiment, the oxygen barrier layer is a sheet disposed between the polyacrylamide gel and the cassette walls. In even yet another such embodiment, the oxygen barrier layer is a film adhering to the surfaces.

In some embodiments of the combination, the means for inhibiting oxygen access to the polyacrylamide gel through the cassette walls comprise an oxygen scavenger embedded within the matrix. The oxygen scavenger can be, for example, a hydroxyl-functionalized polybutadiene oligomer, a crystalline polycondensation product of a meta-xylylene diamine and adipic acid, or a nylon 6 nanocomposite.

In some embodiments, the matrix plastic is styrene-acrylonitrile polymer, polyethylene terephthalate, glycol-modified polyethylene terephthalate, polyethylene naphthalate, or polycarbonate.

An additional combination of a polyacrylamide gel and a plastic cassette in which the polyacylamade gel resides is also provided. In the additional combination, the plastic cassette includes: cassette walls enclosing a gel cavity and including a matrix plastic that is permeable to oxygen; and, a material including either (i) an oxygen barrier layer covering walls of the cassette, (ii) an oxygen scavenger embedded within the matrix, or (iii) both (i) and (ii), wherein the material inhibits oxygen access to the polyacrylamide gel through the cassette walls.

In some embodiments, the material includes an oxygen barrier layer covering walls of the cassette. In one such embodiment, the oxygen barrier layer covers surfaces of the cassette walls that are in contact with the polyacrylamide gel. In another such embodiment, the oxygen barrier layer is a layer of polyvinylidene chloride, low-density polyethylene, or an acrylonitrile methyl acetate copolymer. In yet another such embodiment, the oxygen barrier layer has an oxygen permeability at 25° C. and 100% RH of $5 \times 10^{-10}$ [$cm^3$ cm]/[$cm^2$ s (cm Hg)] or less. In still another such embodiment, the oxygen barrier layer is a sheet disposed between the polyacrylamide gel and the cassette walls. In even yet another such embodiment, the oxygen barrier layer is a film adhering to the surfaces of the cassette walls.

In some embodiments where the material includes an oxygen barrier layer, the walls of the cassette are formed by injection molding and the oxygen barrier layer is applied to the walls of the cassette by in-mold decoration. In some embodiments, the oxygen barrier layer includes a first sublayer and a second sublayer, the first sublayer in contact with the cassette wall and the second sublayer in contact with the polyacrylamide gel, and the second sublayer inhibits oxygen access to the polyacrylamide gel.

In some embodiments of the additional combination, the material includes an oxygen scavenger embedded within the matrix. The oxygen scavenger can be, for example, a hydroxyl-functionalized polybutadiene oligomer, a crystalline polycondensation product of a meta-xylylene diamine and adipic acid, or a nylon 6 nanocomposite.

In some embodiments, the matrix plastic is styrene-acrylonitrile polymer, polyethylene terephthalate, glycol-modified polyethylene terephthalate, polyethylene naphthalate, or polycarbonate.

Also provided herein is a method for casting a polyacrylamide gel from acrylamide monomer in a plastic cassette having cassette walls, which include a matrix plastic that is permeable to oxygen, while inhibiting exposure of the acrylamide monomer to polymerization-inhibiting oxygen. The method includes the steps of: (a) either (i) covering walls of the cassette with an oxygen barrier layer, and casting the polyacrylamide gel in the cassette with the walls so covered, (ii) using a plastic material with an oxygen scavenger substance incorporated therein as the matrix plastic, or (iii) both (i) and (ii); and (b) casting a polyacrylamide gel from an acrylamide monomer solution in the plastic cassette.

In some embodiments, the method includes covering all surfaces of the cassette walls that will be in contact with the acrylamide monomer with an oxygen barrier layer prior to placing the acrylamide monomer in the cassette, and casting the polyacrylamide gel in the cassette with the surfaces so covered. In one such embodiment, the oxygen barrier layer is a layer of polyvinylidene chloride, low-density polyethylene, or an acrylonitrile methyl acetate copolymer. In another such embodiment, the oxygen barrier layer has an oxygen permeability at 25° C. and 100% RH of $5 \times 10^{-10}$ [$cm^3$ cm]/[$cm^2$ s (cm Hg)] or less. In yet another such embodiment, the oxygen barrier layer is a sheet disposed between the polyacrylamide gel and the surfaces. In still another such embodiment, the oxygen barrier layer is a film adhering to the surfaces.

In some embodiments, the method includes using as the matrix plastic a plastic material with an oxygen scavenger incorporated therein. The oxygen scavenger can be, for example, a hydroxyl-functionalized polybutadiene oligomer, a crystalline polycondensation product of a meta-xylylene diamine and adipic acid, or a nylon 6 nanocomposite.

In some embodiments of the method, the matrix plastic is styrene-acrylonitrile polymer, polyethylene terephthalate, glycol-modified polyethylene terephthalate, polyethylene naphthalate, or polycarbonate.

Further provided herein is an additional method for casting a polyacrylamide gel from acrylamide monomer in a plastic cassette having cassette walls, which include a matrix plastic that is permeable to oxygen, while inhibiting exposure of the acrylamide monomer to oxygen. The method includes the steps of: (a) either (i) covering walls of the cassette with an oxygen barrier layer, (ii) using a plastic material with an oxygen scavenger substance incorporated therein as the matrix plastic, or (iii) both (i) and (ii); and (b) casting the polyacrylamide gel from an acrylamide monomer solution in the plastic cassette.

In some embodiments, the additional method includes covering surfaces of the cassette walls that will be in contact with the acrylamide monomer with an oxygen barrier layer prior to placing the acrylamide monomer in the cassette, and casting the polyacrylamide gel in the cassette with the surfaces so covered. In one such embodiment, the oxygen barrier layer is a layer of polyvinylidene chloride, low-density polyethylene, or an acrylonitrile methyl acetate copolymer. In another such embodiment, the oxygen barrier layer has an oxygen permeability at 25° C. and 100% RH of $5 \times 10^{-10}$ [$cm^3$ cm]/[$cm^2$ s (cm Hg)] or less. In yet another such embodiment, the oxygen barrier layer is a sheet disposed between the polyacrylamide gel and the surfaces, or a film adhering to the surfaces.

In some embodiments, the additional method includes using as the matrix plastic a plastic material with an oxygen scavenger incorporated therein. The oxygen scavenger can be, for example, a hydroxyl-functionalized polybutadiene oligomer, a crystalline polycondensation product of a meta-xylylene diamine and adipic acid, or a nylon 6 nanocomposite.

In some embodiments of the additional method, the matrix plastic is styrene-acrylonitrile polymer, polyethylene terephthalate, glycol-modified polyethylene terephthalate, polyethylene naphthalate, or polycarbonate.

These and other features, objects, advantages, and embodiments will be apparent from the description that follows.

BRIEF DESCRIPTIONS OF THE DRAWINGS

FIG. 1 compares protein separation and resolution in two polyacrylamide gels, which were cast in cassettes having walls covered with different oxygen barrier layers. For the 'test' gel, the interior surfaces of the cassette walls were covered with Bicor film. For the 'control' gel, the interior surfaces of the cassette walls were coated with SARAN.

DETAILED DESCRIPTION OF SELECTED EMBODIMENTS

In embodiments utilizing an oxygen barrier layer over walls of the cassette, the layer can be placed over either the inner surfaces, i.e., those in contact with the monomer solution and thus the gel once the monomer is polymerized, the outer surfaces, i.e., those on the exterior of the cassette, or both the inner and outer surfaces. In many cases, the most efficient results will be achieved by placing the layer only over the inner surfaces of the cassette, such that the layer will be in direct contact with the monomer solution and the gel once formed. The layer itself can be a non-adhering plate or sheet that is placed inside the cassette cavity as an insert, or a flexible film or sheet that adheres to the cassette wall surface. In either case, the oxygen barrier material can constitute the entire layer or it can be a coating on one or both sides of the layer. The thickness of the layer or the amount or density of the oxygen barrier material can vary, depending of the choice of material and the option of the manufacturer, and in some cases the size and dimensions of the cassette. A thickness that will not compromise the thickness of the gel being cast to any extent that will affect the performance, and particularly the reproducibility, of the gel will most likely be preferred. For a plate or sheet insert, effective results in many cases will be obtained with a minimum thickness range of about 0.025 mm, or a thickness within the range of about 0.025 mm to about 1 mm. For a film coated on the surface of the cassette, effective results will often be obtained with a thickness range of about 0.001 mm to about 0.03 mm, or from about 0.002 mm to about 0.005 mm.

The oxygen barrier material when used can be any material that significantly inhibits, or at least sharply reduces, the passage of molecules of oxygen gas through the layer, and may or may not achieve this inhibition by combining or forming a complex with the oxygen atoms. The oxygen barrier material may be a material that selectively inhibits the passage of oxygen relative to other gases present in the atmosphere, or one that inhibits all atmospheric gases. The oxygen barrier material will thus be a material of low oxygen permeability, which can be expressed as a permeability coefficient P defined as a fraction with the numerator being the product of the amount of permeate and the film thickness of the material, and the denominator being the product of the surface area of the film, the exposure time, and the pressure drop across the film, all for a given temperature and relative humidity (RH). The units can therefore be expressed as $[cm^3 \, cm]/[cm^2 \, s \, (cm \, Hg)]$, and in many cases, effective results will be obtained with a value of P at 25° C. and 100% RH of about $5 \times 10^{-10} \, [cm^3 \, cm]/[cm^2 \, s \, (cm \, Hg)]$ or less, or from about $0.001 \times 10^{-10}$ to about $5 \times 10^{-10} \, [cm^3 \, cm]/[cm^2 \, s \, (cm \, Hg)]$, and in some cases from about $0.005 \times 10^{-10}$ to about $1 \times 10^{-10} \, [cm^3 \, cm]/[cm^2 \, s \, (cm \, Hg)]$. Optimal barrier materials also possess other properties, notably inertness to the gel components and to all species that will pass through the gel during electrophoresis experiments, such as the biomolecules and the various buffer solutions. Optimal materials will also be those that are able to maintain such inertness over the range of conditions encountered in electrophoresis experiments, notably the pH levels for loading, elution, and washing, and any temperature increases caused by the electric current. Examples of oxygen barrier materials are polyvinylidene chloride, low-density polyethylene, acrylonitrile methyl acetate copolymers, ethylene vinyl alcohol, metallized polyethylene terephthalate, melamine, silica, and alumina. Product names of certain illustrative oxygen barrier materials are SARAN® (Dow Chemical Company, Midland, Mich., USA) (either polyvinylidene chloride or low-density polyethylene) and BAREX® (INEOS USA LLC, Newark, Del., USA). Disclosures of oxygen barrier materials are found in Matlack et al. U.S. Pat. No. 5,175,238 (Dec. 29, 1992), and Rhee et al. U.S. Pat. No. 7,427,430 (Sep. 23, 2008).

In some embodiments, the oxygen barrier layer can be formed on a cassette wall surface during injection molding of the cassette wall. In a technique called in-mold decoration, the barrier layer can be pressed against an interior surface of the mold, where it is held by electrostatic forces or other adhesion forces. The mold is then filled (injected) with molten matrix plastic, which adopts the geometry of the mold cavity before cooling and hardening into the cassette wall. The surface of the barrier layer exposed to the mold cavity is thus joined directly to the matrix plastic of the cassette wall as the plastic cools. On the other hand, the surface of the barrier layer pressed against the interior surface of the mold faces outward when the cassette wall is removed from the mold. This surface of the barrier layer can come into direct contact with the gel monomer solution when two cassette walls are paired together for gel casting.

In some embodiments, the oxygen barrier layer includes multiple materials sandwiched together, as in sublayers, one of which is an oxygen barrier material. Such an oxygen barrier layer can be made from, for example, Bicor™ (ExxonMobil Chemical Company, Houston, Tex., USA), a film that comprises a polypropylene core coated on one side with acrylic and on the other side with polyvinylidene chloride (an oxygen barrier material). When injection molding the cassette wall, the mold can be decorated with the barrier layer to affix the barrier layer to the cassette wall and control how the sublayer containing the oxygen barrier material is oriented with respect to the cassette wall. This in turn can determine how this sublayer is oriented with respect to the gel that the cassette will hold. For example, Bicor film can be placed in an injection mold with the acrylic coating facing the mold cavity and the polyvinylidene chloride coating pressed against the interior surface of the mold. Molten matrix plastic can then be injected into the mold according to standard methods to form the cassette wall. In this configuration, the Bicor acrylic coating is joined to (or in contact with) the matrix plastic of the cassette wall and the polyvinylidene chloride coating faces away from the matrix plastic. Two such cassette walls can be paired together in a cassette, with the polyvinylidene chloride coming into direct contact with the monomer solution as the gel is cast.

In general, oxygen barrier layers or materials can be applied to the cassette walls as desired, and methods of doing so are not limited to in-mold decoration. For example, an oxygen barrier layer can be coated, glued, bonded, or welded to the surface of a cassette wall after the cassette wall has cooled from injection molding, or is otherwise fully formed. Alternatively, the barrier layer and cassette wall can be formed with complementary protrusions or indentations, such as interlocking teeth or hooks, allowing the two surfaces, otherwise mostly flat, to be coupled mechanically. The oxygen barrier layer can also adhere to the cassette wall through surface tension, static electricity, or any other force that can be readily harnessed. However, such adherence is not required in all embodiments for the oxygen barrier layer to cover the cassette wall and inhibit oxygen access to the polyacrylamide gel in the cassette. In some embodiments, the oxygen barrier layer covers the cassette wall but does not adhere to it, and is simply inserted between the cassette wall and gel cavity.

Among methods of applying an oxygen barrier layer to the surface of a cassette wall, in-mold decoration offers advantages over methods that require treatment (for example coating or bonding) of a pre-formed cassette wall. One advantage is convenience: the oxygen barrier layer can be applied at the same time the cassette wall is injection-molded, rather than requiring a separate application step after injection molding. In-mold decoration can also provide greater uniformity in the composition and thickness of the oxygen barrier layer, across the area of this layer that will be in contact with acrylamide monomer solution inside the cassette. Such uniformity can result in more uniform permeability of the oxygen barrier layer to oxygen and, in turn, more uniform pore sizes in a gel resulting from polymerization of the monomer solution.

In embodiments utilizing an oxygen scavenger embedded within the matrix plastic that forms the walls of the cassette, the oxygen scavenger will often be an oxidizable substance that consumes oxygen in a classic oxidation reaction. Notable among such substances are those for which the oxidation reaction is induced or initiated by exposure to humidity in addition to the oxygen. Many such scavengers include a transition metal catalyst, an example of which is cobalt. Examples of oxygen scavenging substances are hydroxyl-functionalized polybutadiene oligomers, crystalline polycondensation products of a meta-xylylene diamine and adipic acid, and nylon 6 nanocomposites. Product names of certain illustrative oxygen scavenging substances are AMOSORB® (Amoco Chemicals, Chicago, Ill., USA), POLYSHIELD® (INVISTA North America S.a.r.l., Wilmington, Del., USA), AEGIS® (Honeywell International Inc., Morristown, N.J., USA), OXBAR® (Constar International Inc., Philadelphia, Pa., USA), ValOR™ (The Valspar Corporation, Pittsburgh, Pa., USA), and DiamondClear (Constar International Inc., Philadelphia, Pa., USA). Disclosures of oxygen scavenger substances are found in Cahill et al. U.S. Pat. No. 6,083,585 (Jul. 4, 2000), Akkapeddi et al. U.S. Pat. No. 6,656,993 (Dec. 2, 2003, Deshpande et al. U.S. Pat. No. 7,691,290 (Apr. 6, 2010), and Deshpande et al. U.S. Pat. No. 7,994,245 (Aug. 9, 2011). The concentration of the oxygen scavenger in the plastic matrix can vary widely, and optimal concentrations are readily determinable by routine experimentation involving the observation and testing of polyacrylamide gels formed in cassettes that are made of the materials. In most cases, effective results will be obtained with concentrations ranging from about 1% to about 10%, and often about 2% to about 8%, by weight.

The base or matrix plastic of which the cassette walls are constructed, other than the oxygen barrier or oxygen scavenger material added to or embedded in the base or matrix plastic, can be any of a variety of plastic materials. Examples are styrene-acrylonitrile polymer, polyethylene terephthalate, glycol-modified polyethylene terephthalate, polyethylene naphthalate, and polycarbonate. The concepts disclosed herein, as noted above, are particularly useful for slab gel cassettes, of which a typical construction consists of two plates conveniently formed by injection molding, then arranged parallel to each other and joined together at two side edges by adhesives or various forms of welding, with spacers between the plates to form a slab-shaped cavity for the gel and removable strips along the top and bottom edges of the cavity, the strips serving to retain the monomer solution during casting of the gel and yet being removable to allow access of electrode buffers to the upper and lower edges of the gel during electrophoresis. Such cassettes are made in a variety of sizes to accommodate both large and small slab gels.

Gels are cast in the cassettes by conventional methods. In cases in which an oxygen barrier layer is placed over the walls of the cassette, the method may involve first covering the surfaces of the cassette walls that will be in contact with the acrylamide monomer solution with an oxygen barrier layer, prior to placing the solution in the cassette. The monomer solution is then placed in the cassette together with any other components needed to cause polymerization to occur, and the gel is then formed by allowing the monomer to polymerize. In cases in which an oxygen scavenger is embedded within the matrix plastic that forms the walls of the cassette, the cassette itself is most conveniently formed by injection molding, using a plastic resin that contains the oxygen scavenger. Once the cassette is formed, the monomer solution and any other components needed to cause polymerization to occur are placed in the cassette, and the gel is then formed by polymerization. The performance of an electrophoresis experiment in the cassette-supported gel is conducted according to conventional procedures, notably those for SDS-PAGE, which do not need any special adjustments for use with the cassettes and gels described herein.

Example

Cassette walls for electrophoresis gel cassettes were prepared using two methods. Cassettes were then assembled from the cassette walls, and gels cast in the cassettes were compared for their ability to separate and resolve proteins.

In method 1, the cassette walls were prepared by injection molding styrene-acrylonitrile (SAN) polymer, using Bicor™ 210 ASB-X film as an in-mold decoration. The Bicor film was placed in the mold such that the acrylic coating was facing the mold cavity and the polyvinylidene chloride coating was pressed against the interior surface of the mold. Upon injection molding, the Bicor film became affixed to the plastic of the cassette wall, with the acrylic coating in contact with the SAN plastic and the polyvinylidene chloride coating facing away from the plastic.

In method 2, the cassette walls were prepared by injection molding SAN without an in-mold decoration. After injection molding, the walls were allowed to cool and harden, and were then coated with SARAN® latex (SERFENE™ 400; Dow Chemical Company, Midland, Mich., USA), which was applied in liquid form and heat-cured.

Cassettes were assembled from the cassette walls prepared according to methods 1 and 2. In the cassette corresponding to method 1, the Bicor film served as the oxygen barrier layer. In the cassette corresponding to method 2, the SARAN® coating served as the oxygen barrier layer. Both cassettes were assembled such that surfaces of the cassette walls that were covered with the oxygen barrier layer faced inward and would be in contact with gels cast inside the cassettes.

A 12% Tris-HCl gel was hand-cast in each cassette from an acrylamide monomer solution. Protein standards (Bio-Rad Laboratories, Inc., Hercules, Calif., USA) and *E. coli* cell lysate were run on both gels, and the gels were visualized using standard methods (FIG. 1). Protein bands were at least as sharp and well resolved in the gel corresponding to method 1 as they were in the gel corresponding to method 2. This result suggests that, when used as an oxygen barrier layer covering a cassette wall, a Bicor film is at least as effective as a SARAN coating in inhibiting the access of oxygen to the gel during casting.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A combination of a polyacrylamide gel and a plastic cassette in which said polyacrylamide gel resides, the plastic cassette comprising:
   cassette walls enclosing a gel cavity and comprising a matrix plastic that is permeable to oxygen, and
   a material comprising an oxygen barrier layer covering walls of said cassette such that the oxygen barrier layer is in contact with said polyacrylamide gel, wherein the walls of the cassette are formed by injection molding and the oxygen barrier layer is applied to the walls of the cassette by in-mold decoration,
   wherein the material inhibits oxygen access to the polyacrylamide gel through the cassette walls.

2. The combination of claim 1 wherein said oxygen barrier layer is a layer of a member selected from the group consisting of polyvinylidene chloride and low-density polyethylene.

3. The combination of claim 1 wherein said oxygen barrier layer has an oxygen permeability at 25° C. and 100% RH of $5\times10^{-10}$ [cm$^3$ cm]/[cm$^2$ s (cm Hg)] or less.

4. The combination of claim 1 wherein the material further comprises an oxygen scavenger embedded within said matrix.

5. The combination of claim 4 wherein said oxygen scavenger is a member selected from the group consisting of a hydroxyl-functionalized polybutadiene oligomer, a crystalline polycondensation product of a meta-xylylene diamine and adipic acid, and a nylon 6 nanocomposite.

6. The combination of claim 1 wherein said matrix plastic is a member selected from the group consisting of styrene-acrylonitrile polymer, polyethylene terephthalate, glycol-modified polyethylene terephthalate, polyethylene naphthalate, and polycarbonate.

7. A method for casting a polyacrylamide gel from acrylamide monomer in a plastic cassette having cassette walls comprising a matrix plastic that is permeable to oxygen while inhibiting exposure of said acrylamide monomer to oxygen, said method comprising:
   (a) providing said cassette, wherein said cassette is made by covering walls of said cassette that will be in contact with said polyacrylamide gel with an oxygen barrier layer, wherein the walls of the cassette are formed by injection molding and the oxygen barrier layer is applied to the walls of the cassette by in-mold decoration; and
   (b) casting said polyacrylamide gel from an acrylamide monomer solution in said plastic cassette.

8. The method of claim 7 wherein said oxygen barrier layer is a layer of a member selected from the group consisting of polyvinylidene chloride and low-density polyethylene.

9. The method of claim 7 wherein said oxygen barrier layer has an oxygen permeability at 25° C. and 100% RH of $5\times10^{-10}$ [cm$^3$ cm]/[cm$^2$ s (cm Hg)] or less.

10. The method of claim 7 wherein said matrix plastic further comprises an oxygen scavenger incorporated therein.

11. The method of claim 10 wherein said oxygen scavenger is a member selected from the group consisting of a hydroxyl-functionalized polybutadiene oligomer, a crystalline polycondensation product of a meta-xylylene diamine and adipic acid, and a nylon 6 nanocomposite.

12. The method of claim 7 wherein said matrix plastic is a member selected from the group consisting of styrene-acrylonitrile polymer, polyethylene terephthalate, glycol-modified polyethylene terephthalate, polyethylene naphthalate, and polycarbonate.

* * * * *